United States Patent
Marx et al.

(10) Patent No.: US 6,355,454 B1
(45) Date of Patent: Mar. 12, 2002

(54) PROCESS FOR THE FERMENTATIVE PRODUCTION OF L-AMINO ACIDS USING CORYNEFORM BACTERIA

(75) Inventors: Achim Marx; Bettina Mockel, both of Bielefeld; Walter Pfefferle, Halle; Hermann Sahm, Julich, all of (DE); Albert De Graaf, Heerlen (NL); Lothar Eggeling, Julich (DE)

(73) Assignee: Degussa Huls AG, Hanau (DE)

( * ) Notice: Subject to any disclaimer, the term of this patent is extended or adjusted under 35 U.S.C. 154(b) by 0 days.

(21) Appl. No.: 09/324,940

(22) Filed: Jun. 3, 1999

(30) Foreign Application Priority Data

Feb. 20, 1999 (DE) .......................................... 199 07 347

(51) Int. Cl.$^7$ ............................................... C12P 13/04
(52) U.S. Cl. ....................................................... 435/106
(58) Field of Search .......................................... 435/106

(56) References Cited

FOREIGN PATENT DOCUMENTS

| EP | 0 358 940 | 3/1990 |
|----|-----------|--------|
| EP | 0 435 132 | 7/1991 |
| FR | 2 575 492 | 7/1986 |
| WO | WO 99 46363 | 9/1999 |

OTHER PUBLICATIONS

Bormann et al. Molecular analysis of the Corynebacterium glutamicum gdh gene encoding glutamate dehydrogenase. Molecular Microbiology (1992) 6(3):317–326.*

Sahm et al. Construction of L–Lysne, L–Threonine, or L–Isoleucine–Overproducing Strains of Corynebacterium glutamicum. Annals New York Academy of Sciences (1996) 782:25–39.*

Snedecor et al. Selection, Expression, and Nucleotide Sequencing of the Glutamate Dehydrogenase Gene of *Peptostreptococcus asaccharolyticus*. Journal of Bacteriology (Oct. 1991) 173(19): 6162–6167.*

English language translation of portions of reference LR submitted with IDS filed Oct. 23, 2001: Marx et al., "Bestimmung des Kohlenstoffflusses im Zentralstoffwechsel von Corynebacterium glutamicum mittels 13C–isotopenanalyse", Berichte des Forschungszentrums Juelich, No. 3459, 1997, pg. 1, line 19–33; page 7, table 1, page 61, line 1 to page 77, line 20, page 99, lines 1–5 and 10–16.

Marx et al., "Response of the central metabolism in Corynebacterium glutamicum to the use of an NADH–dependent glutamate dehydrogenase.", Metabolic Engineering, vol. 1, Nr. 1, Jan. 1999, pp. 35–48.

Marx et al., "Bestimmung des Kohlenstoffflusses im Zentralstoffwechsel von Corynebacterium glutamicum mittels 13C–isotopenanalyse", Berichte des Forschungszentrums Juelich, No. 3459, 197, pp.1–99 (in German).

Kramer, "Genetic and physiological approaches for the production of amino acids", Journal of Biotechnology, vol. 45, Nr. 1, Feb. 1996, pp. 1–21.

English language abstract of DR above.

English language abstract of ER above.

* cited by examiner

*Primary Examiner*—Ponnathapu Achutamurthy
*Assistant Examiner*—Kathleen Kerr
(74) *Attorney, Agent, or Firm*—Pillsbury Winthrop LLP

(57) ABSTRACT

This invention relates to a process for the production of L-amino acids using coryneform bacteria, in which the glutamate dehydrogenase gene is amplified.

6 Claims, No Drawings

PROCESS FOR THE FERMENTATIVE PRODUCTION OF L-AMINO ACIDS USING CORYNEFORM BACTERIA

CROSS-REFERENCE TO RELATED APPLICATION

This application claims priority from German Application No. 199 07 347.3, filed on Feb. 20, 1999.

BACKGROUND OF THE INVENTION

1. Field of the Invention

The present invention provides a process for the fermentative production of L-amino acids using coryneform bacteria, in which the glutamate dehydrogenase gene is amplified.

2. Background Information

L-Amino acids are used in animal nutrition, human medicine and the pharmaceuticals industry.

L-Amino acids are produced by fermentation using strains of coryneform bacteria which produce L-amino acids, in particular using *Corynebacterium glutamicum*. Due to the significance of this group of products, efforts are constantly being made to improve the production process. Improvements to the process may relate to measures concerning fermentation technology, for example stirring and oxygen supply, or to the composition of the nutrient media, such as for example sugar concentration during fermentation, or to working up of the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites, such as for example the lysine analogue S-(2-aminoethyl)cysteine, or are auxotrophic for regulatorily significant amino acids and produce L-amino acids.

For some years, methods of recombinant DNA technology have also been used to improve strains of *Corynebacterium glutamicum* which produce L-amino acids by amplifying individual biosynthesis genes and investigating the effect on L-amino acid production. Review articles on this subject may be, found inter alia in Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Jetten and Sinskey (Critical Reviews in Biotechnology 15, 73–103 (1995)) and Sahm et al. (*Annuals of the New York Academy of Science* 782, 25–39 (1996)).

The enzyme glutamate dehydrogenase catalyses the reductive amination of α-ketoglutaric acid to yield glutamic acid. French published patent application 2 575 492 describes a DNA fragment from *Corynebacterium melassecola* 801 which bears a glutamate dehydrogenase gene. It is possibly used therein to increase glutamic acid production in the fermentation of *Corynebacterium melassecola*. The nucleotide sequence of the glutamate dehydrogenase gene of *Corynebacterium glutamicum* ATCC13032 has been described by Börmann et al. (*Molecular Microbiology* 6, 317–326 (1992)). The nucleotide sequence of the glutamate dehydrogenase gene of *Peptostreptococcus asaccharolyticus* is stated in Snedecor et al. (*Journal of Bacteriology* 193, 6162–6167 (1991)).

SUMMARY OF THE INVENTION

The inventors set themselves the object of providing novel measures for the improved fermentative production of other L-amino acids.

DESCRIPTION OF THE INVENTION

L-Amino acids are used in animal nutrition, human medicine and the pharmaceuticals industry. There is accordingly general interest in providing improved processes for the production of L-amino acids.

When L-amino acids are mentioned below, they are intended to mean the protein-forming amino acids L-lysine, L-threonine, L-isoleucine, L-valine, L-proline, L-tryptophan and optionally the salts thereof and also L-homoserine, in particular L-lysine, L-threonine and L-tryptophan.

The present invention provides a process for the fermentative production of L-amino acids using coryneform bacteria, which in particular already produce the corresponding L-amino acids and in which the nucleotide sequence coding for the enzyme glutamate dehydrogenase is amplified, in particular overexpressed.

Preferred embodiments are stated in the claims.

In this connection, the term "amplification" describes the increase in the intracellular activity of one or more enzymes in a microorganism, which enzymes are coded by the corresponding DNA, for example by increasing the copy number of the gene or genes, by using a strong promoter or a gene which codes for a corresponding enzyme having elevated activity and optionally by combining these measures.

The microorganisms provided by the present invention are capable of producing L-amino acids from glucose, sucrose, lactose, fructose, maltose, molasses, starch, cellulose or from glycerol and ethanol. The microorganisms may comprise representatives of the coryneform bacteria in particular of the genus Corynebacterium. Within the genus Corynebacterium, *Corynebacterium glutamicum* may in particular be mentioned, which is known in specialist circles for its ability to produce L-amino acids. Suitable strains of the genus Corynebacterium, in particular of the species *Corynebacterium glutamicum*, are the known wild type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and mutants or strains produced therefrom, such as for example the L-lysine producing strains

*Corynebacterium glutamicum* FERM-P 1709
*Brevibacterium flavum* FERM-P 1708 and
*Brevibacterium lactofermentum* FERM-P 1712, or the L-threonine producing strains

*Corynebacterium glutamicum* FERM-P 5835
*Brevibacterium flavum* FERM-P 4164 and
*Brevibacterium lactofermentum* FERM-P 4180, or the L-isoleucine producing strains

*Corynebacterium glutamicum* FERM-P 756
*Brevibacterium flavum* FERM-P 759 and
*Brevibacterium lactofermentum* FERM-P 4192 or the L-valine producing strains

*Brevibacterium flavum* FERM-P 512 and
*Brevibacterium lactofermentum* FERM-P 1845, and the L-tryptophan producing strains

*Corynebacterium glutamicum* FERM-BP 478
*Brevibacterium flavum* FERM-BP 475 and

*Brevibacterium lactofermentum* FERM-P 7127. It is noted that Corynebacterium and Brevibacterium are both considered to be corynebacteria in the state of the art at the time the invention was made. Furthermore, *Corynebacterium glutamacin* and *Brevibacterium lactofermentum* were considered to be the same species.

The inventors discovered that, after overexpression of L-glutamate dehydrogenase, coryneform bacteria produce L-amino acids in an improved manner, wherein L-glutamic acid is not claimed here.

The glutamate dehydrogenase gene of *C. glutamicum* described by Börmann et al. (*Molecular Microbiology* 6, 317–326 (1992)) may be used according to the invention. The glutamate dehydrogenase gene from other microorganisms, such as for example that from *Peptostreptococcus asaccharolyticus*, which has been described by Snedecor et al. (*Journal of Bacteriology* 173, 6162–6167 (1991)), is also suitable. Alleles of the stated genes arising from the degeneracy of the genetic code or from functionally neutral sense mutations may also be used.

Overexpression may be achieved by increasing the copy number of the corresponding genes, or the promoter and regulation region located upstream from the structural gene may be mutated. Expression cassettes incorporated upstream from the structural gene act in the same manner. It is additionally possible to increase expression during fermentative L-amino acid production by means of inducible promoters. Expression is also improved by measures to extend the lifetime of the mRNA. Enzyme activity is moreover amplified by preventing degradation of the enzyme protein. The genes or gene constructs may either be present in plasmids in a variable copy number or be integrated in the chromosome and amplified. Alternatively, overexpression of the genes concerned may also be achieved by modifying the composition of the nutrient media and culture conditions.

The person skilled in the art will find guidance in this connection inter alia in Martin et al. (*Bio/Technology* 5, 137–146 (1987)), in Guerrero et al. (*Gene* 138, 35–41 (1994)), Tsuchiya and Morinaga (*Bio/Technology* 6, 428–430 (1988)), in Eikmanns et al. (*Gene* 102, 93–98 (1991)), in European patent EPS 0 472 869, in U.S. Pat. No. 4,601,893, in Schwarzer and Pühler (*Bio/Technology* 9, 84–87 (1991), in Reinscheid et al. (*Applied and Environmental Microbiology* 60, 126–132, (1994)), in LaBarre et al. (*Journal of Bacteriology* 175, 1001–1007 (1993)), in patent application WO 96/15246, in Jensen and Hammer (*Biotechnology and Bioengineering* 58, 191–195 (1998)), in Makrides (*Microbiological Reviews* 60:512–538 (1996)) and in known textbooks of genetics and molecular biology.

Examples of plasmids by means of which glutamate dehydrogenase may be overexpressed are pEK1.9gdh-1 and pEKExpgdh, which are present in strains ATCC13032/pEK1.9gdh-1 and DH5α/pEKExpgdh. Plasmid pEK1.9gdh-1 is a shuttle vector, which contains the NAD-dependent glutamate dehydrogenase gene of *C. glutamicum*. Plasmid pEKExpgdh is a shuttle vector, which contains the NAD-dependent glutamate dehydrogenase gene of *Peptostreptococcus asaccharolyticus*.

It may additionally be advantageous for the production of the corresponding L-amino acids to overexpress one or more enzymes of the particular amino acid biosynthesis pathway as well as glutamate dehydrogenase. Thus, for example

- the dapA gene which codes for dihydrodipicolinate synthase may additionally be overexpressed in order to improve L-lysine producing coryneform bacteria (EP-B 0197335),
- the gene which codes for acetohydroxy acid synthase may additionally be overexpressed in order to improve L-valine producing coryneform bacteria (EP-B 0356739),
- the gene which codes for anthranilic acid phosphoribosyl transferase may additionally be overexpressed in order to improve L-tryptophan producing coryneform bacteria (EP-B 0124048),
- the gene which codes for homoserine dehydrogenase may additionally be overexpressed in order to improve coryneform bacteria which produce L-homoserine or L-threonine or L-isoleucine (EP-A 0131171).

It may furthermore be advantageous for the production of the corresponding L-amino acid to switch off unwanted secondary reactions in addition to overexpressing glutamate dehydrogenase (Nakayama: "Breeding of Amino Acid Producing Micro-organisms", in: Overproduction of Microbial Products, Krumphanzl, Sikyta, Vanek (eds.), Academic Press, London, UK, 1982).

For the purposes of L-amino acid production, the microorganisms according to the invention may be cultivated continuously or discontinuously using the batch process or the fed batch process or repeated fed batch process. A summary of known cultivation methods is given in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must adequately satisfy the requirements of the particular strains. Culture media for various microorganisms are described in "Manual of Methods for General Bacteriology" from American Society for Bacteriology (Washington D.C., USA, 1981). Carbon sources which may be used include sugars and carbohydrates, such as for example glucose, sucrose, lactose, fructose, maltose, molasses, starch and cellulose, oils and fats, such as for example soya oil, sunflower oil, peanut oil and coconut oil, fatty acids, such as for example palmitic acid, stearic acid and linoleic acid, alcohols, such as for example glycerol and ethanol, and organic acids, such as for example acetic acid. These substances may be used individually or as a mixture. Nitrogen sources which may be used comprise organic compounds containing nitrogen, such as peptone, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are potassium dihydrogen phosphate or dipotassium hydrogen phosphate or the corresponding salts containing sodium. The culture medium must furthermore contain metal salts, such as for example magnesium sulfate or iron sulfate, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during cultivation.

Basic compounds, such as sodium hydroxide, potassium hydroxide, ammonia, or acidic compounds, such as phosphoric acid or sulfuric acid, are used appropriately to control the pH of the culture. Antifoaming agents, such as for example fatty acid polyglycol esters, may be used to control foaming. Suitable selectively acting substances, such as for example antibiotics, may be added to the medium in order to maintain plasmid stability. Oxygen or gas mixtures containing oxygen, such as for example air, are introduced into the culture in order to maintain aerobic conditions. The temperature of the culture is normally from 20° C. to 45° C.

and preferably from 25° C. to 40° C. The culture is continued until a maximum quantity of the desired L-amino acid has been formed. This objective is normally achieved within 10 hours to 160 hours.

L-Amino acids may be analysed automatically using anion exchange chromatography with subsequent ninhydrin derivatisation, as described by Spackman et al. (*Analytical Chemistry*, 30, 1190 (1958)).

The following microorganisms have been deposited with Deutschen Sammlung für Mikrorganismen und Zellkulturen (DSMZ, Mascheroder Weg 1b, D-38124 Braunschweig, Germany) on Jan. 8, 1999 in accordance with the Budapest Treaty:

*Corynebacterium glutamicum* strain ATCC13032/pEK1.9gdh-1 as DSM 12614.

*Escherichia coli* K12 strain DH5α/pEKExpgdh as DSM 12613.

DETAILED DESCRIPTION OF THE INVENTION

The present invention is illustrated in greater detail by the following practical examples.

To this end, testing was performed with amino acid producing strains, in which the superiority of the claimed process is demonstrated:

a) the L-lysine producing strain *Corynebacterium glutamicum* DSM5715, (EP-B- 0435 132) and b) the L-threonine and L-isoleucine producing strain *Brevibacterium flavum* DSM5399 (EP-B- 0385 940) and c) the L-valine producing, isoleucine-requiring strain ATCC13032ΔilvA, which has been deposited as DSM12455 with Deutschen Sammlung für Mikroorganismen und Zellkulturen in Braunschweig (Germany) in accordance with the Budapest Treaty.

EXAMPLE 1
Production of L-amino acid producers with amplified glutamate dehydrogenase Plasmid pEK1.9gdh-1 corresponds to the plasmid pEK1.9gdh described by Börmann et al. (*Molecular Microbiology* 6, 317–326 (1992)). It was isolated from ATCC13032/pEK1.9gdh-1. The known plasmid pEKExpgdh (Marx et al., *Metabolic Engineering* 1, 35–48 (1999)), which bears the glutamate dehydrogenase gene of *Peptostreptococcus asaccharolyticus* (Snedecor et al., *Journal of Bacteriology* 173, 6162–6167 (1991)) was isolated in the same manner from *E. coli* strain DH5α/pEKExpgdh.

Strains DSM5715, DSM5399 and ATCC13032ΔilvA were transformed with plasmid pEK1.9gdh-1 as described by Liebl et al. (*FEMS Microbiology Letters* 65, 299–304 (1989)). The transformants were selected on brain/heart agar from Merck (Darmstadt, Germany) which had been supplemented with 50 mg/l of kanamycin. In this manner, strains DSM5715/pEK1.9gdh-1, DSM5399/pEK1.9gdh-1 and ATCC13032ΔilvA/pEK1.9gdh-1 were obtained. Strain DSM5715 was transformed in the same manner with plasmid pEKExpgdh and strain DSM5715/pEKExpgdh obtained.

EXAMPLE 2
Production of L-lysine

Strain DSM5715/pEK1.9gdh-1 was precultivated in complex medium 2TY consisting of 16 g/l of tryptone, 10 g/l of yeast extract and 5 g/l of NaCl. To this end, 60 ml of medium 2TY, contained in a 500 ml Erlenmeyer flask with 2 flow spoilers, were inoculated with an inoculating loop of the strain and the culture incubated for 12 hours at 150 rpm and 30° C.

In order to inoculate 60 ml of production medium, contained in a 500 ml Erlenmeyer flask with 2 flow spoilers, the preculture was centrifuged for 10 minutes at 5000 rpm in a Sepatech Minifuge RF (Heraeus, Hanau, Germany) centrifuge. The supernatant was discarded and the pellet resuspended in 1 ml of production medium. An aliquot of this cell suspension was added to the production medium, such that an OD600 of approx. 2.0 was obtained. The production medium used was medium CGXII with a pH of 7.0 (Table 1) described by Keilhauer et al. (*Journal of Bacteriology* 175, 5595–5603 (1993)) supplemented with 20 g/l of glucose, 350 mg/l of leucine and 50 mg/l of kanamycin monosulfate. The cultures were incubated for 72 hours at 30° C. and 150 rpm.

TABLE 1

| Component | Concentration per liter |
|---|---|
| $(NH_4)_2SO_4$ | 20 g |
| Urea | 5 g |
| $KH_2PO_4$ | 1 g |
| $K_2HPO_4$ | 1 g |
| $MgSO_4 \cdot 7H_2O$ | 0.25 g |
| 3-Morpholinopropane-sulfonic acid | 42 g |
| $FeSO_4 \cdot 7H_2O$ | 10 mg |
| $MnSO_4 \cdot H_2O$ | 10 mg |
| $ZnSO_4 \cdot 7H_2O$ | 1 mg |
| $CuSO_4$ | 0.2 mg |
| $NiCl_2 \cdot 6H_2O$ | 0.02 mg |
| $CaCl_2$ | 10 mg |
| Protocatechuic acid | 0.03 mg |
| Biotin | 200 µg |

Optical density (OD) (Biochrom Novaspec 4049, LKB Instrument GmbH, Gräfelfing, Germany) was then determined at a measuring wavelength of 600 nm, as was the concentration of L-lysine formed using an amino acid analyser from Eppendorf-BioTronik (Hamburg, Germany) by ion exchange chromatography and post-column reaction with ninhydrin detection. Table 2 shows the result of the test.

TABLE 2

| Strain | OD | L-lysine g/l |
|---|---|---|
| DSM5715 | 16.5 | 4.5 |
| DSM5715/pEK1.9gdh-1 | 19.4 | 6.2 |

EXAMPLE 3
Production of L-threonine and L-isoleucine

Strain DSM5399/pEK1.9gdh-1 was precultivated in complete medium CgIII (Kase & Nakayama, Agricultural and Biological Chemistry 36 (9) 1611–1621 (1972)) with 50 µg/ml of kanamycin. To this end, 10 ml of medium CgIII, contained in a 100 ml Erlenmeyer flask with 4 flow spoilers, were inoculated with an inoculating loop of the strain and the culture incubated for 16 hours at 240 rpm and 30° C.

In order to inoculate 10 ml of production medium, contained in a 100 ml Erlenmeyer flask with 4 flow spoilers, the OD (660 nm) of the preculture was determined. The main culture was inoculated to an OD of 0.1. The production medium used was the medium CgXII described by Keilhauer et al. (*Journal of Bacteriology* 1993, 175: 5595–5603). The composition of the medium is shown in Example 2. 4% of glucose and 50 mg/l of kanamycin sulfate were added. The cells were incubated for 48 hours at 33° C., 250 rpm and 80% atmospheric humidity.

Optical density at 660 nm was then determined, as was the concentration of the L-threonine and L-isoleucine formed as stated in Example 2. Table 3 shows the result of the test.

TABLE 3

| Strain | OD | L-threonine g/l | L-isoleucine g/l |
|---|---|---|---|
| DSM5399 | 10.5 | 1.77 | 1.05 |
| DSM5399/pEK1, 9gdh-1 | 11.0 | 2.26 | 1.44 |

EXAMPLE 4

Production of L-valine

Strain ATCC13032ΔilvA/pEK1.9gdh-1 was precultivated in complete medium CgIII (Kase & Nakayama, Agricultural and Biological Chemistry 36 (9) 1611–1621 (1972)) with 50 µg/ml of kanamycin. To this end, 50 ml of medium CgIII, contained in a 500 ml Erlenmeyer flask with 4 flow spoilers, were inoculated with an inoculating loop of the strain and the culture incubated for 16 hours at 140 rpm and 30° C.

In order to inoculate 60 ml of production medium, contained in a 500 ml Erlenmeyer flask with 4 flow spoilers, the OD (660 nm) of the preculture was determined. The main culture was centrifuged and the supernatant discarded. The pellet was resuspended in 5 ml of production medium and the main culture inoculated to an OD of 0.3. The production medium used was medium CgXII (Keilhauer et al., *Journal of Bacteriology* 1993 175: 5595–5603) as described in Example 3 (with 4% glucose). The cells were incubated for 48 hours at 30° C., 150 rpm.

Optical density at 660 nm was then determined, as was the concentration of L-valine formed as described as stated in Example 2. Table 4 shows the result of the test.

TABLE 4

| Strain | OD | L-valine g/l |
|---|---|---|
| ATCC13032ΔilvA | 18.5 | 0.29 |
| ATCC13032ΔilvA/pEK1.9gdh-1 | 17.6 | 0.45 |

EXAMPLE 5

Production of L-lysine, L-valine and L-alanine

Strain DSM5715/pEKExpgdh was precultivated in complex medium 2TY consisting of 16 g/l of tryptone, 10 g/l of yeast extract and 5 g/l of NaCl. To this end, 60 ml of medium 2TY, contained in a 500 ml Erlenmeyer flask with 2 flow spoilers, were inoculated with an inoculating loop of the strain and the culture incubated for 12 hours at 150 rpm and 30° C.

In order to inoculate 60 ml of production medium, contained in a 500 ml Erlenmeyer flask with 2 flow spoilers, the preculture was centrifuged for 10 minutes at 5000 rpm in a Sepatech Minifuge RF (Heraeus, Hanau, Germany) centrifuge. The supernatant was discarded and the pellet resuspended in 1 ml of production medium. An aliquot of this cell suspension was added to the production medium such that an OD600 of approx. 0.4 was obtained. The production medium used was medium CGC (table 5) described by Schrumpf et al. (*Journal of Bacteriology* 173, 4510–4516 (1991)), supplemented with 25 g/l of glucose, 350 mg/l of leucine, 42 g/l of 3-morpholinopropanesulfonic acid and 50 mg/l of kanamycin monosulfate at pH 7. The cultures were incubated for 30 hours at 30° C. and 150 rpm.

TABLE 5

| Component | Concentration per liter |
|---|---|
| $(NH_4)_2SO_4$ | 5 g |
| Urea | 5 g |
| $KH_2PO_4$ | 0.5 g |
| $K_2HPO_4$ | 0.5 g |
| $MgSO_4 \cdot 7H_2O$ | 0.25 g |
| $FeSO_4 \cdot 7H_2O$ | 10 mg |
| $MnSO_4 \cdot H_2O$ | 10 mg |
| $ZnSO_4 \cdot 7H_2O$ | 1 mg |
| $CuSO_4$ | 0.2 mg |
| $NiCl_2 \cdot 6H_2O$ | 0.02 mg |
| $CaCl_2 \cdot 2H_2O$ | 10 mg |
| Biotin | 200 µg |

Optical density (OD) (Biochrom Novaspec 4049, LKB Instrument GmbH, Gräfelfing, Germany) was then determined at a measuring wavelength of 600 nm, as was the concentration of L-alanine, L-lysine and L-valine formed using an amino acid analyser from Eppendorf-BioTronik (Hamburg, Germany) by ion exchange chromatography and post-column reaction with ninhydrin detection. Table 6 shows the result of the test.

TABLE 6

| Strain | OD | L-Alanine g/l | L-lysine g/l | L-valine g/l |
|---|---|---|---|---|
| DSM5715 | 29.4 | Traces | 1.6 | 0.1 |
| DSM5715/pEKExpgdh | 19.4 | 0.6 | 2.1 | 0.6 |

What is claimed is:

1. A process for the fermentative production of one or more L-amino acids selected from the group consisting of L-lysine, L-threonine, L-isoleucine, L-valine, L-proline, L-tryptophan and L-homoserine, said process comprising:

a) fermenting coryneform bacteria producing at least one of the L-amino acids, in which bacteria at least a nucleotide sequence encoding glutamate dehydrogenase is overexpressed;

b) accumulating at least one of the L-amino acids in the medium or in the cells of the bacteria; and c) isolating the L-amino acid(s).

2. The process according to claim 1, wherein said nucleotide sequence encodes a bacterial glutamate dehydrogenase endogenous to coryneform bacteria.

3. The process according to claim 1, wherein said nucleotide sequence encodes a glutamate dehydrogenase that is NADP dependent.

4. The process according to claim 1, wherein said nucleotide sequence encodes a glutamate dehydrogenase that is NAD dependent.

5. The process according to claim 1, wherein bacteria transformed with plasmid vector pEK.9gdh-1, deposited in *Corynebacterium glutamicum* under accession number DSM 12614, are used.

6. The process according to claim 1, wherein bacteria transformed with plasmid vector pEKExpgdh, deposited in *Corynebacterium glutamicum* under accession number DSM 12613, are used.

* * * * *